(12) United States Patent
Zhang et al.

(10) Patent No.: US 7,557,089 B2
(45) Date of Patent: Jul. 7, 2009

(54) USE OF DERIVATIVES OF SUCCINATE ESTERS FOR THE TREATMENT OF DEMENTIA

(75) Inventors: Jianjun Zhang, Beijing (CN); Jiangong Shi, Beijing (CN); Yafang Wang, Beijing (CN); Dan Zhang, Beijing (CN); Mei Gao, Beijing (CN); Yongchun Yang, Beijing (CN); Shengyang Huang, Beijing (CN)

(73) Assignee: Institute of Materia Medica, Chinese Academy of Medical Science, Beijing (CN)

( * ) Notice: Subject to any disclaimer, the term of this patent is extended or adjusted under 35 U.S.C. 154(b) by 0 days.

(21) Appl. No.: 10/541,082

(22) PCT Filed: Dec. 31, 2003

(86) PCT No.: PCT/CN03/01155

§ 371 (c)(1),
(2), (4) Date: Apr. 7, 2006

(87) PCT Pub. No.: WO2004/058244

PCT Pub. Date: Jul. 15, 2004

(65) Prior Publication Data

US 2006/0281692 A1 Dec. 14, 2006

(30) Foreign Application Priority Data

Dec. 31, 2002 (CN) .................... 02 1 59342

(51) Int. Cl.
A61K 31/70 (2006.01)
A61K 31/7028 (2006.01)
A61K 31/7034 (2006.01)
C07H 15/04 (2006.01)

(52) U.S. Cl. .............. 514/25; 514/23; 536/4.1
(58) Field of Classification Search .......... 514/25, 514/23; 536/4.1
See application file for complete search history.

(56) References Cited

OTHER PUBLICATIONS

Kizu et al. (Chemical & Pharmaceutical Bulletin (1999) vol. 47, No. 11, pp. 1618-1625).*
Huang et al. (Yaoxue Xuebao (2002), vol. 37, No. 3, pp. 199-203) (Abstract Sent).*
Wu et al. (Planta medica (Aug. 1996) vol. 62, No. 4, pp. 317-321) (Abstract Sent.*
Li et al. (Zhongguo Gonggong Weisheng (2002), 18 (3), 284-286) (Abstract Sent).*
Huang et al. Studies on the chemical constituents of Coeloglossum viride (L.) Hartm. var. bracteatum (Willd.) Richter Institute of Chinese Materia Medica, Chinese Academy of Traditional Chinese Medicine, Beijing 100700, China. Yao Xue Xue Bao. Mar. 2002;37(3):199-203.
Huang SY, Shi JG, Yang YC, Hu SL. Studies on chemical constituents from Tibetan medicine wangla(rhizome of Coeloglossum viride var. bracteatum) Institute of Materia Medica, Chinese Academy of Medical Sciences, Beijing 100050, China. Zhongguo Zhong Yao Za Zhi. Feb. 2002;27(2):118-20.

* cited by examiner

*Primary Examiner*—Shaojia Anna Jiang
*Assistant Examiner*—Michael C Henry
(74) *Attorney, Agent, or Firm*—Townsend and Townsend and Crew LLP

(57) ABSTRACT

The use of extract form Wangla (*coeloglossum viride* (L) Hartm. Var. *Bracteatum* (Willd.) Richter), succinate derivative esters, and a derivative and pharmaceutical acceptable salts thereof, for the manufacture of a pharmaceutical preparation for the treatment of dementia, particularly for the treatment of Alzheimer' disease and Vascular dementia. Through Animal experiment, it has been demonstrated that, succinate derivative esters can improve learning and memory ability in dementia rats induced by scopolamine and cyclohexenyl imine; improve learning and memory ability in dementia rats induced by β-amyloid; improve learning and memory ability in dementia rats induced by permanent ligation of bilateral carotid; and improve memory ability of normal animals. It has the advantage of high activity, low toxicity and no inhibition to cholinesterase.

10 Claims, 4 Drawing Sheets

Figure 1:
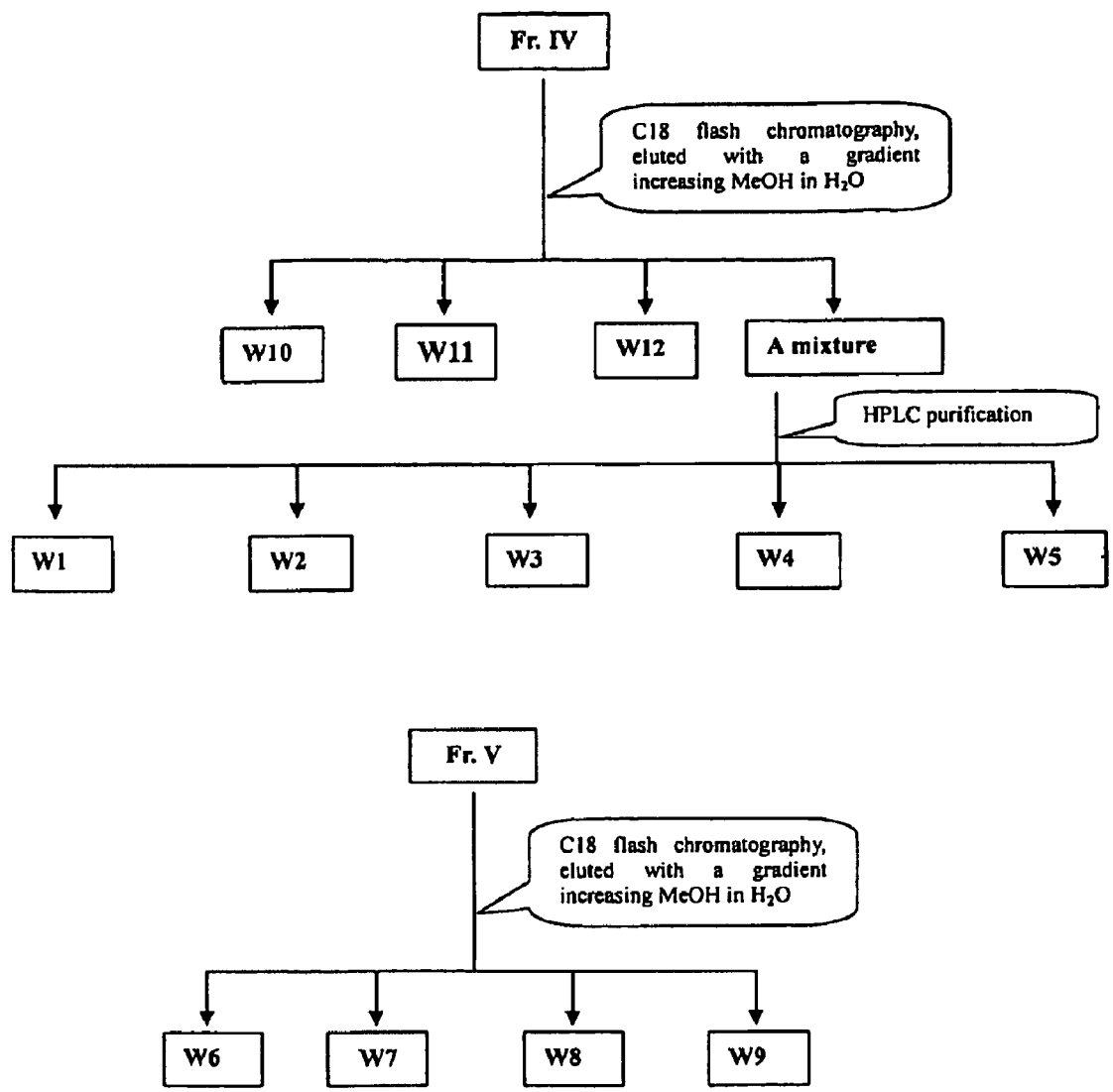

Figure 1. Flowchart of extraction and isolation from Wangla
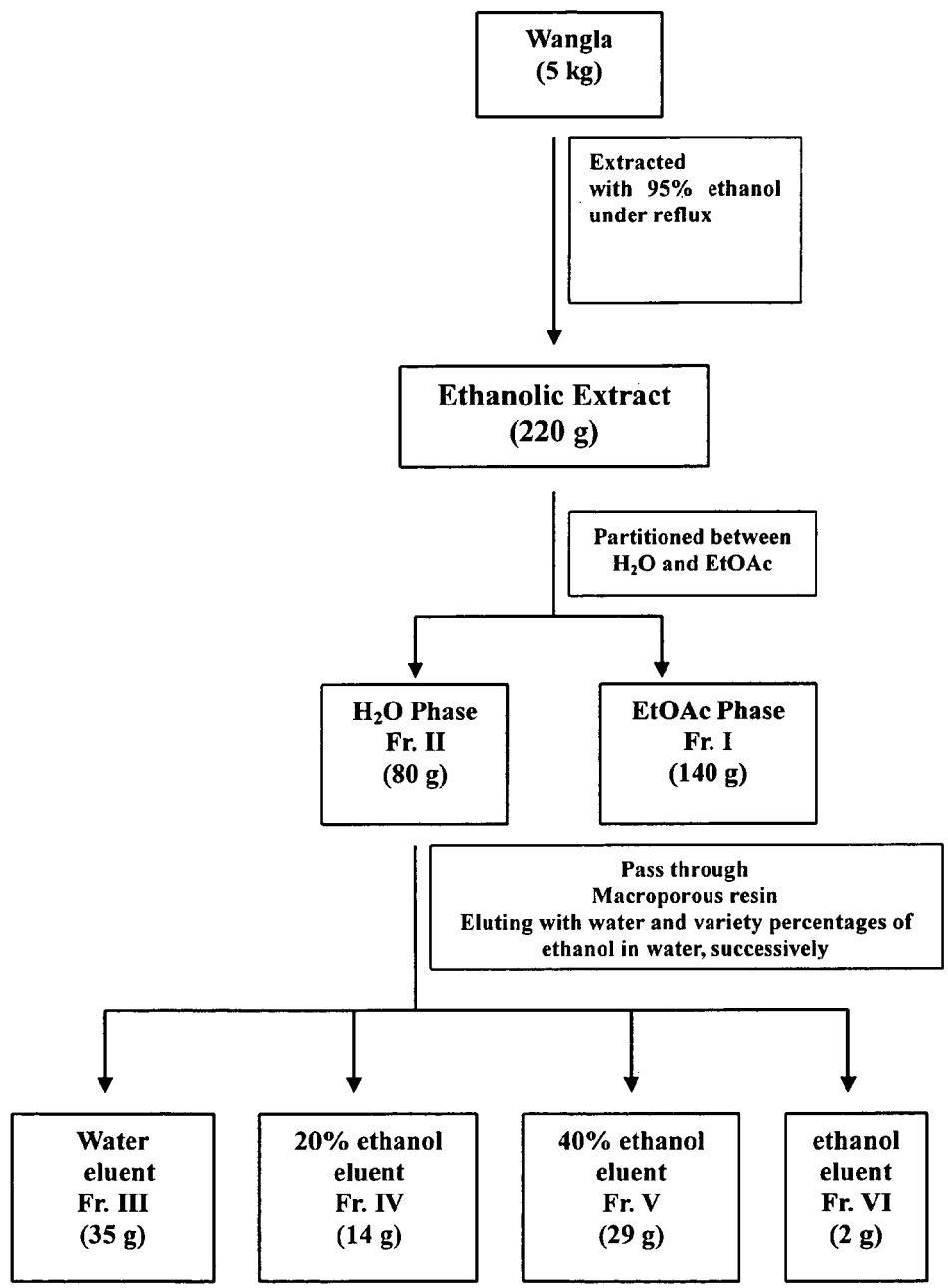

USE OF DERIVATIVES OF SUCCINATE ESTERS FOR THE TREATMENT OF DEMENTIA

FIELD OF THE INVENTION

The present invention is related to the use of an extract containing derivatives of succinate esters from Wangla (*Coeloglossum viride* (L) Hartm. Var. *Bracteatum* (Wild.) Richter), synthetic derivatives of succinate esters, and pharmaceutical acceptable salts thereof in the manufacture of a pharmaceutical preparation for the treatment of dementia, particularly for the treatment of Alzheimer' disease and vascular dementia.

BACKGROUND OF THE INVENTION

At present, the average life-span in China is over 70 years old. Predicted by a scientific research abroad, by year 2025 there will be 18.8% persons over 65 years old. This data indicates that, 20 years later, there will be one elder in every 5 people. Alzheimer's Disease tends to occur in people older than 50 years. Multi-infarct dementia or senile dementia due to cerebrovascular pathological changes occurs in people older than 60 years. As the world's population grows older, the incidence of Alzheimer's Disease and Senile Dementia is expected to increase. The ageing and the peculiar neurological degenerative diseases-different kinds of dementia will go through two types of death, first in spirit, then in physical. It does not only afflict the patients, but also brings burden to their families and the society. The aging population is considered to be an adverse factor impacting social development and stability, only inferior to battles, plague, starvation and shortage in resource.

Dementia is an acquired and durative intellective obstacle syndromes caused by brain function impediment that includes cognitive decline, impaired memory, language, thinking, behaviour, and abnormal personality. Dementia mainly includes Alzheimer's Disease, Vascular Dementia, and etc. The pathological changes of Alzheimer's Disease involve the formation of senile plaques-mostly made of a component called Aβ (β-amyloid peptide), the loss of cholinergic neurons and the deposition of Aβ in endotheliocyte of the blood vessels, etc. Vascular Dementia is induced by cerebrovascular diseases, mostly ischemia. The pathological changes involve multiple lacunae illness or large-scale infarct and atherosclerotic changes. Recent studies indicate that vascular factors participate in the process of Senile Dementia and the lack of blood flow in brain is the most risky factor.

There are many kinds of drugs for preventing ageing and treating Senile Dementia. At present, the leading remedies applied clinically are cholinergic drugs and Acetylcholinerase inhibitors (ChEIs), accompanied with adjuvant treatment on improvement of cerebrovascular circulation and protection of brain, yet the effect is limited. Among the drugs increasing cholinergic system function, only Ach precursor show mild therapeutical effect. Although Ach receptor agonists and ChEIs have certain effects, the duration is too short and the adverse effects are relatively great. Cerebrovascular dilation drugs help in energy supply and intellectual improvement by enhancing the brain blood supply, but the really valuable drugs for cerebrovascular dilation must have high selectivity, meanwhile, they will not affect brain metabolism and 'pilfer blood', and they have anti-aggregating of blood platelet and anti-thrombus effect. Nimodipine, a Calcium antagonist, qualifies some of the above criteria, but it only acts on L-type voltage-gated $Ca^{2+}$ channel and has no effects on N-type and T-type $Ca^{2+}$ channels. Some neuropeptides and NGF were deemed to be promising in the treatment of dementia, but their clinical trail results were discouraging, primarily attribute to be hard to pass the blood-brain barrier (BBB) and exert their actions in brain. Since 2-pyrrolidone acetamide (trade name Piracetam) came into use, there is no doubt that it is a new nootropic in the early reports. It is recently reported at home and abroad, it has mild effect or does not act on all kinds of memory impairments and senile dementia. It is a water soluble compound and has a low permeance through BBB, and it is difficult to be concentrated to the target to exert its effect.

*Coeloglossum viride* (L.) Hartm. Var. *bracteatum* (Willd.) Richter is widely distributed, mainly in the west of China such as Tibet, Inner Mongolia, Shanxi, Gansu, Qinghai, etc. The dried rhizome of *Coelogrlossum viride* (L.) Hartm. var. *bracteatum* is the famous Tibetan medicine named Wangla, having a long history of use in minority in the west of china. The indications were multiple, such as invigorating vital energy, promoting the production of body fluid, tranquilizing and enhancing intelligence.

Through the preliminary biological activity screening of this plant, we found that the ethanolic extract of the rhizome of this plant has preferable intellectual improvement, sedation and anti-fatigue activities, which is consistent with its indications. Based on the results, we investigated systematically the chemical component and biological activity of this plant, and several derivatives of succinate mono- and di-esters were isolated and identified. The chemical components of *Coeloglossum viride* (L.) Hartm. var. *bracteatum* (Willd.) Richter have been published by the inventors, but the biological activities of the extract and purified compounds have not been reported. (See: Huang Sheng-Yang, Shi Jian-Gong, Yang Yun-Chun, Hu Shi-lin, Studies on the Chemical Constituents of *Coeloglossu viride* (L) Harm. var. *bracteatum* (Willd) Richter., *Acta Pharmaceutica Sinica*, 2002, 37(3), 199-203; Sheng Yang HUANG, Jian Gong SHI, Yong Chun YANG, Shi Lin HU. Two new isobutyltartrate monoesters from *Coeloglossum viride* (L.) Hartm. var. *bracteatum* (Willd.) Richter. Chinese Chemical Letters, 2002, 13(6):551-554.)

DETAILED DESCRIPTION OF THE INVENTION

To overcome the shortage of the prior art, the object of the present invention is to provide a method for the treatment of dementia, particularly for the treatment of Alzhimer's disease and Vascular dementia by using an extract containing derivatives of succinate esters from Wangla (*Coeloglossum viride* (L) Hartm. Var. *Bracteatum* (Wild.) Richter), and synthetic derivatives of succinate esters defined by formula I.

Another object of the present invention is to provide a pharmaceutical composition, which comprises derivatives of succinate ester of formula (I) as active component and pharmaceutically acceptable carrier.

The compounds of the present invention include its derivatives, stereo-isomers and pharmaceutically acceptable salts.

The object of the present invention is to provide the use of the extract of *Coelogrossum viride* (L.) Hartm. var. *bracteatum* (wild.) Richter in the manufacture of a medicament for the treatment of dementia, particularly for the treatment of Alzheimer's disease and vascular dementia.

Another object of the invention is to provide a pharmaceutical composition comprising the extract of *Coeloglossum viride* (L.) Hartm. Var. *bracteatum* (Wild.) Richter as active component, and pharmaceutically acceptable carrier.

Particularly, the present invention is related to the compounds of formula (I):

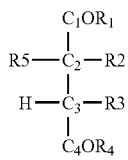
(I)

wherein:

$R_1$ and $R_4$ are selected from —$OCH_3$, —OH, —O-Glu,

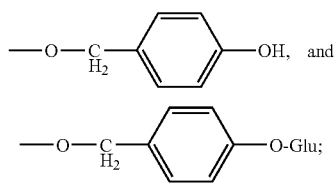
OH, and

O-Glu;

$R_2$ and $R_3$ are selected from H, —OH, —O-Glu,

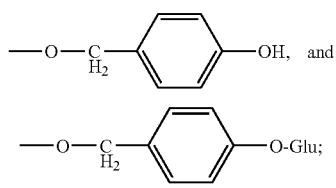
OH, and

O-Glu;

$R_5$ is selected from non-branched or branched $C_{1-6}$ alkyl, preferably, from methyl, ethyl, propyl, isopropyl, n-butyl, isobutyl, tert-butyl, more preferably, from isopropyl, tert-butyl, and isobutyl;

The configuration of the chiral centers at C-2 and C-3 are 2R3S, 2R3R, 2S3S and 2S3R respectively.

In order to achieve the aim of this invention, the preferable structures include but not limited to:

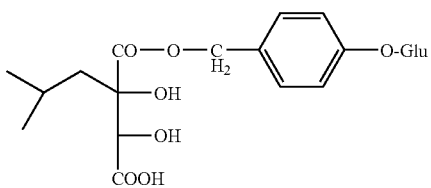

1-(4-β-D-glucopyranosyloxybenzyl)-2-isobutyltartrate (Coelovirin A) (W1)

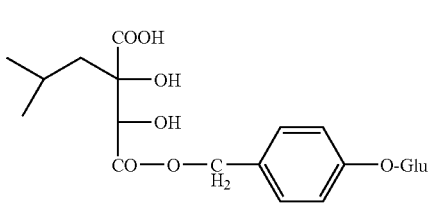

4-(4-β-D-glucopyranosyloxybenzyl)-2-isobutyltartrate (Coelovirin B) (W2)

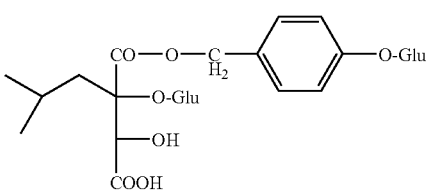

1-(4-β-D-glucopyranosyloxybenzyl)-2-β-D-glucopyranosyl-2-isobutyltartrate (Coelovirin C) (W3)

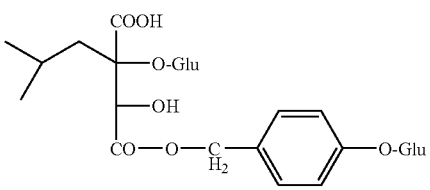

4-(4-β-D-glucopyranosyloxybenzyl)-2-β-D-glucopyranosyl-2-isobutyltartrate (Coelovirin D) (W4)

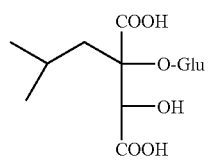

2-β-D-glucopyranosyl-2-isobutyltartrate (W5)

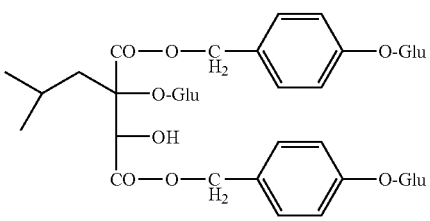

1,4-bis(β-D-glucopyranosyloxybenzyl)-2-β-D-glucopyranosyl-2-isobutyltartrate (Dactylorhin B) (W6)

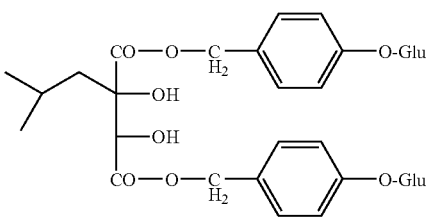

1,4-bis(β-D-glucopyranosyloxybenzyl)-2-isobutyl-
tartrate (Loroglossin) (W7)

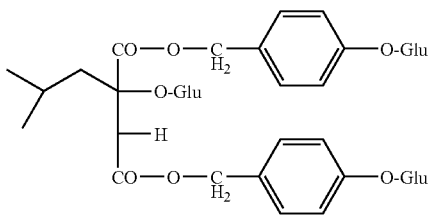

1,4-bis(β-D-glucopyranosyloxybenzyl)-2-β-D-glu-
copyranosyl-2-isobutylmalate (Dactylorhin A) (W8)

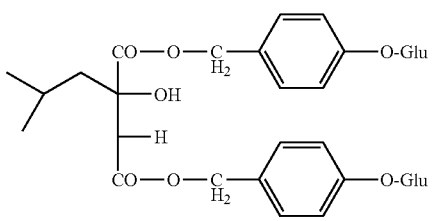

1,4-bis(β-D-glucopyranosyloxybenzyl)-2-hydroxy-2-
isobutylmalate (militarine) (W9)

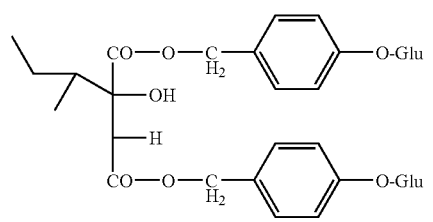

1,4-bis(β-D-glucopyranosyloxybenzyl)-2-hydroxy-2-
(butan-2-yl)-malate (W10)

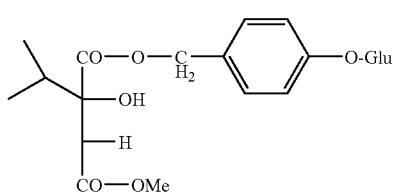

1-(β-D-glucopyranosyloxybenzyl)-2-hydroxy-2-
isopropyl-malate methyl ester (W11)

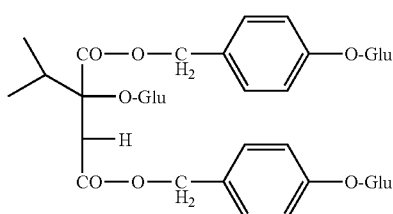

1,4-bis(β-D-glucopyranosyloxybenzyl)-2-β-D-glu-
copyranosyl-2-isopropyl-malate (W12)

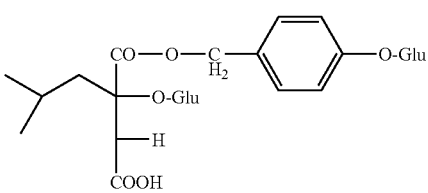

1-β-D-glucopyranosyloxybenzyl-2-β-D-glucopyra-
nosyl-2-isobutylmalate (W13)

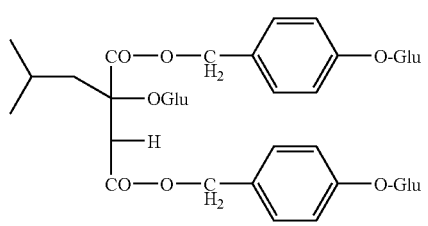

1,4-bis(β-D-glucopyranosyloxybenzyl)-2-β-D-glu-
copyranosyl-2-isopropyl-malate (W14)

Tested on the animal model for the impaired acquisition of learning caused by scopolamine, at very low dosage, the extract and the compounds of the present invention treatment are able to prolong significantly the step-down latency and decrease the number of errors in the test session. These results indicate that the extract and the compounds of the invention can effectively ameliorate scopolamine-induced impaired acquisition of learning in mice.

ICV injection of Aβ (1-42) impaired learning and memory function, treatment of mice and rats with the extract and the compounds of the present invention significantly blocked the Aβ (1-42)-induced impairment in passive avoidance performance, also significantly improved Aβ (1-42)-induced decrease in spatial working memory. These findings suggest that the extract and the compounds of the invention may have preventive effect against memory impairment related with Aβ of Alzheimer's disease.

It is well known that chronic cerebral hypoperfusion induced by permanent occlusion of bilateral common carotid arteries in animal is associated with behavioral and histopathological alterations. Cerebral hypoperfusion in mice and rats caused deficits of learning and memory. Long term treatment with the extract and the compounds of the present invention significantly alleviated these changes in behavioral (step-down testing and water-maze testing). Our data suggest the beneficial role of the extract and the compounds of the present invention in the cerebrovascular insufficiency states and dementia.

Tested on cycloheximide (an inhibitor of protein synthesis) induced mice dementia model, the extract and the compounds of the present invention significantly reversed the cycloheximide-induced reduction of step-through latency, and decreased the number of errors in the test session. The result indicates that the extract and the compounds of the present invention can ameliorate impairment of passive avoidance induced by cycloheximide, and increase learning and memory performance of mice.

To investigate the influence of the extract of the invention on the memory in normal mice, we found that the extract of the invention treatment shortened the escape latency of mice in water-maze testing, and the number of errors is decreased significantly. The result indicates that the extract of the invention can enhance the capacity of learning and memory in normal mice.

In the experiment of detecting the acetylcholinesterase (AChE) activity in vivo, we found that a single dose or multiple doses of the extract and the compounds of the invention to mice or rats have no inhibition on activity of ACHE in animal brain. It indicates that the improvement mechanism of the extract and the compounds of the invention on cognitive function in animal is not mediated via anticholinesterase pathway.

The result of an acute toxicity study in mice showed that no significant differences in mice behavior were observed, and there was no animal death and the body weight of mice grown as normal mice after orally administered a single dose of 5 g/kg of the extract or the compounds of the invention. It suggests that the extract or the compounds of the invention have a very low acute toxicity in mice.

The pharmacological studies demonstrated that the extract or the compounds of the invention have effects on treatment of dementia, particularly Alzheimer disease and vascular dementia, as well as mild cognition imparment in the early stage of dementia, deterioration of mental faculties and amnesia, etc. In addition, the extract and the compounds of the invention has a very low toxicity, high safety and no inhibition on activity of ACHE in animal brain.

The present invention is also related to a pharmaceutical composition made by mixing any of the extract and the compounds of the invention used as active component and commonly used drug excipients and/or additives. Normally, a pharmaceutical composition contains from 0.1 to 95 wt % of the extract or the compounds of the invention.

The pharmaceutical composition of the present invention can be made according to the well known method in the art. For this purpose, if necessary, any of the extract and the compounds of the invention may be mixed with one of more commonly used drug excipients and/or additives in the form of solid or liquid. The composition may be formulated into the form for the administration use of human or veterinary.

The extract or the compounds of the invention or pharmaceutical composition thereof may be formulated into the unit dosage form. The compounds can be administered by a variety of routes including oral, rectal, transdermal, peritoneal, subcutaneous, intravenous, intramuscular, oral mucosal and intranasal. It is preferred to be orally administrated.

The extract or the compounds of the invention or pharmaceutical composition thereof may be adminsitrated by injecting, such as intravenously, intramuscularly, subcutaneously and intracutaneously injecting.

The dosage may be in liquid form or solid form. As for the liquid form, it may be a true solution, a colloid, a microparticle, an emulsion and a suspension. The other dosage form may be tablets, capsules, drops, pills, aerosols, powders, sulitions, suspentions, emulsions, particles, suppositories, and froze-dried powder for injection. The extract or compositions of the invention can be formulated into common formulation, sustained released formulation, controled released formulation, target formulation or various microparticle systems.

For preparing solid compositions such as tablets, various carriers well known in the art may be employed. Some examples of suitable carriers include: diluent and absorbent, such as starches, dextrin, calcium sulphate, lactose, mannitol, sucrose, sodium chloride, glucose, urea, calcium carbonate, kaolin, microcrystalline cellulose, aluminium silicate; wetting agents and binders, such as water, glycerol, polyethylene glycol, ethanol, propanol, starch paste, dextrin, syrup, honey, glucose solution, gum acacia paste, gelatin paste, sodium carboxymethylcellulose, lakh, methyl cellulose, potassium phosphate, and polyvinylpyrrolidone; disintergrating agent, such as dry starch, alginates, agarose, laminaran, sodium bicarbonate, citric acid, calcium carbonate, polyoxyethylene sorbitan fatty acid ester, sodium dodecyl sulphate, methylcellulose, ethylcellulose; disintegration inhibitor, such as sucrose, tristearin, cacao butter, hydrogenated oil; sorbefacient, such as quaternary ammonium salt, lauryl sodium sulfate; lubricating agents, such as talc, silica, corn starch, salt stearate, boric acid, liquid petrolatum, polyethylen glycol. The tablets of the present invention may be coated, such as sugar coating, film coating, enteric coating, or coated by two layers or multiple layers.

For preparing pills, various carriers well known in the art may be used. The examples of such carriers are diluents and absorbents, such as glucose, lactose, starch, cacao butter, hydrogenated plant oil, polyvinylpyrrolidone, Gelucire, kaolin, talc; binders, such as gum acacia, gum tragacanth, gelatin, ethanol, honey, liquid sugar, rice paste or flour paste; disintergrating agent, such as agarose powder, dry starch, alginates, sodium dodecyl sulphate, methyl cellulose, ethyl cellulose.

For preparing capsules, the extract or compound of the present invention is mixed with the various carriers mentioned above, and put the result mixture in hard or soft gelatin capsule. Also the compound of the present invention can be made into microcapsule, suspensed in the aquatic medium as suspension, encapsulated into hard capsules or be made into injections.

For example, the extract or compound of the invention may be made into injectable formulations, such as solution, suspension, emulsion and froze-dried powder. Such formulation may be aqueous or non-aqueous, and may contain one and/or more pharmaceutically acceptable carrier, diluent, binder, lubricant, preservative, surfacant or dispersant. The diluent may be selected from water, ethanol, polyethylene glycol, 1,3-propanol, ethoxylated stearyl alcohol, polyoxided isostearyl alcohol, polyoxyethylene sorbitan fatty acid ester, etc.

In addition, in order to prepare isotonic injections, proper amount of NaCl, glucose or glycerol can be added into the injectable formulations. Also routine cosolvent, buffer, pH-adjusting agent and the like can be added. These additives are used frequently in this field.

It is apparent to one skilled in the art that the therapeutically effective dose for active compounds of the invention or a pharmaceutical composition thereof will depend on various factors, such as the property and severity of the diseases to be treated, gender, age, weight, characteristic and individual response of the patients or animals, route and number of the administration, and the treatment purpose. Therefore, the therapeutic dose according to the invention may vary greatly. In general, the dosages to be administrated may be readily determined by those skilled in the art. A therapeutically effective dose for use of the instant extract or compounds of the invention comprises a dose range of from about 0.001 to about 150 mg/kg/day, preferably from 0.01 to about 100 mg/kg/day, in particular from about 0.01 to about 60 mg/kg/day, more particular from about 0.1 to about 10 mg/kg/day of active ingredient. The total daily dosage may be administrated once or in divided doses into two, three or four times daily. It will be understood, however, that the amount of the compound actually administered will be determined by a physician according to his clinical experience and the other therapy concurrently used.

Every remedy's total dosage may be administered once or divided into several times. The extract, compounds, any pharmaceutical composition of the invention may be used solely or combined with other therapeutic drugs with adjusted dosage.

The compounds of the invention exist in the following 6 genera of orchidaceous family, *Coeloglossum, Galeola, Gastrodia, Loroglossum, Orchis, Vanda*. (see table)

Compounds Included in This Invention from Orchidaceous Plants

| No. | Compounds | Molecular formula | Molecular weight | Plant source* |
|---|---|---|---|---|
| 1 | W1 | $C_{21}H_{30}O_{12}$ | 474 | a |
| 2 | W2 | $C_{21}H_{30}O_{12}$ | 474 | a |
| 3 | W3 | $C_{27}H_{40}O_{17}$ | 636 | a |
| 4 | W4 | $C_{27}H_{40}O_{17}$ | 636 | a |
| 5 | W7 | $C_{34}H_{46}O_{18}$ | 742 | a, f, g, h |
| 6 | W6 | $C_{40}H_{56}O_{23}$ | 904 | a, f |
| 7 | W13 | $C_{27}H_{40}O_{16}$ | 620 | a, f |
| 8 | W11 | $C_{21}H_{30}O_{11}$ | 458 | c |
| 9 | W12 | $C_{33}H_{44}O_{17}$ | 712 | b, c |
| 10 | W10 | $C_{34}H_{46}O_{17}$ | 726 | b |
| 11 | W9 | $C_{34}H_{46}O_{17}$ | 726 | f, g |
| 12 | W14 | $C_{40}H_{56}O_{25}$ | 888 | f |

*a: *Coeloglossum viride*; b: *Galeola faberi*; c: *Galeola septentrionalis*; d: *Gastrodia elata*; e: *Loroglossum hircinum*; f: *Orchis latifolia*; g: *Orchis militaris*; h: *Orchis papilionacea*;

ILLUSTRATION OF THE FIGURES

FIG. 1: Flowchart of extraction and isolation from Wangla

Figure 2:
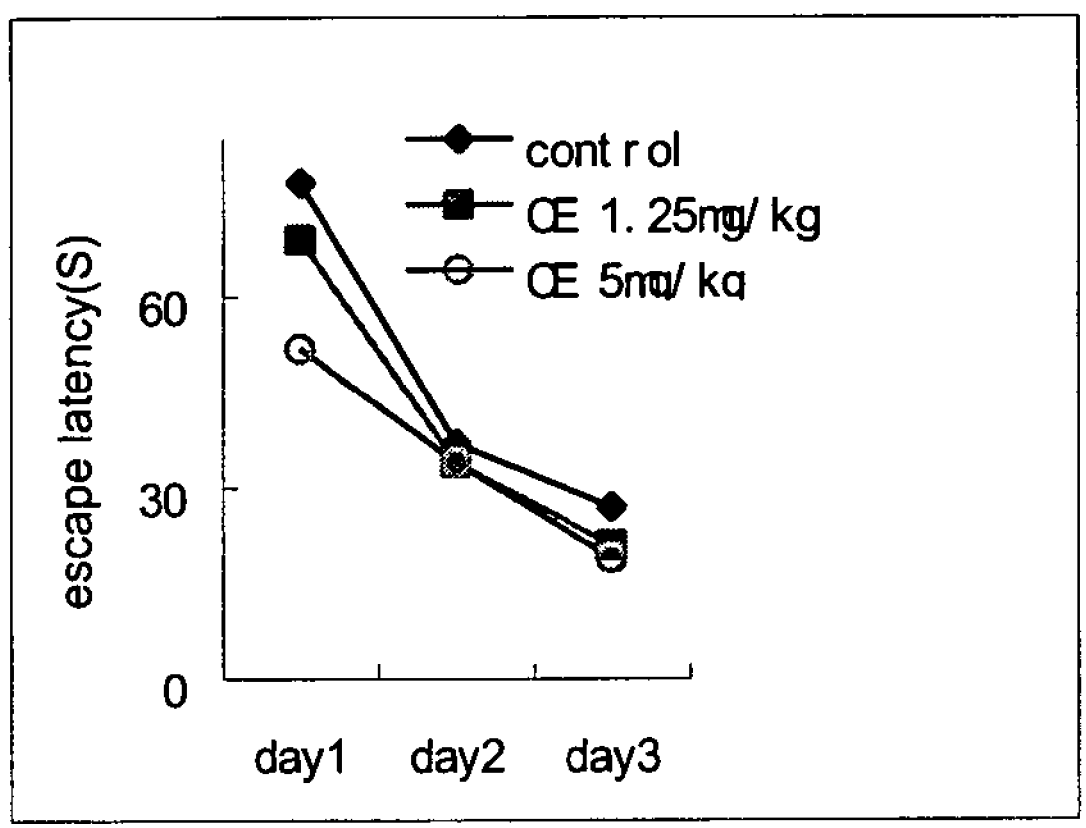

FIG. 2: The time needed for the mice to reach the target region daily

Figure 3:
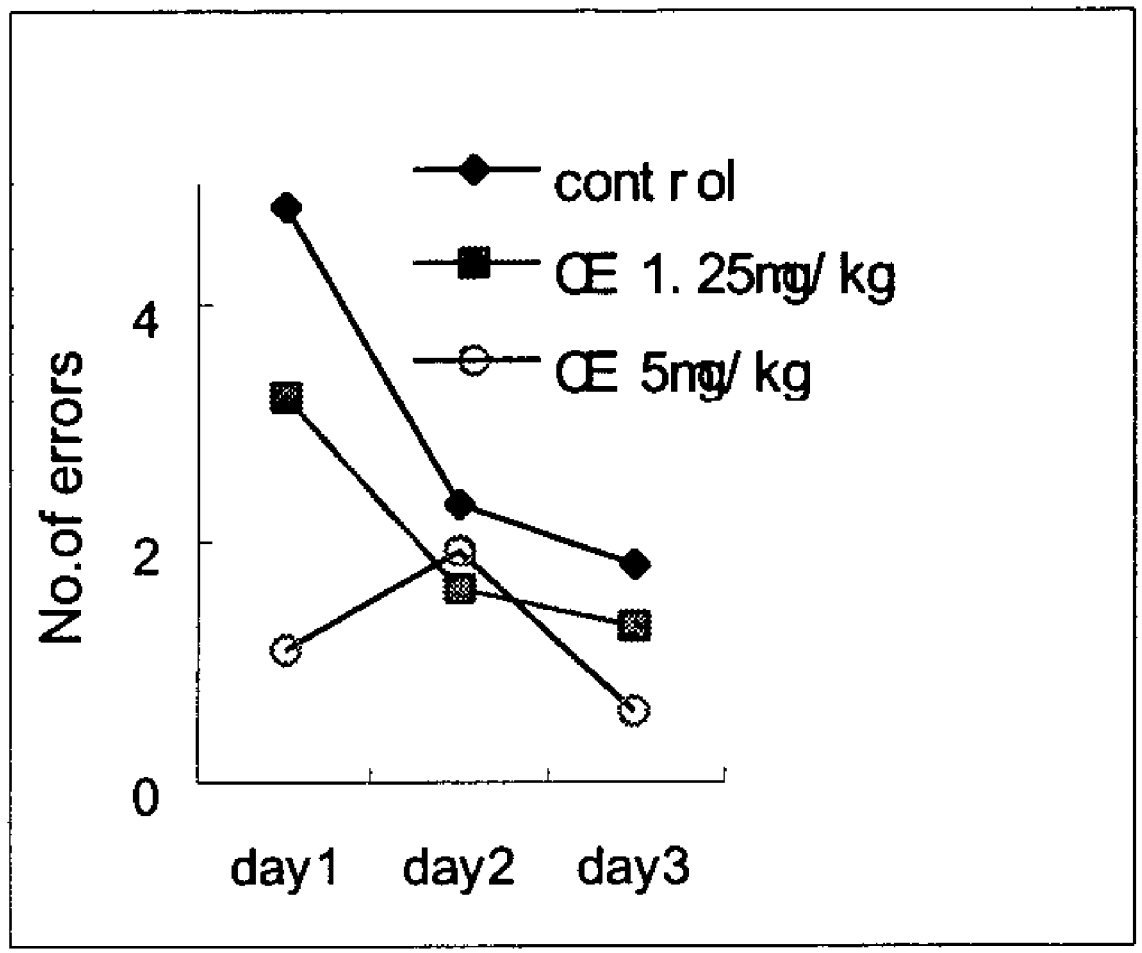

FIG. 3: The error times of the mice daily

EXAMPLES

The following examples are used to illustrate the present invention, but do not mean any limitation to the invention.

CE: An effective fraction extracted from Wangla

W6, W7, W8, W9: effective compounds isolated from CE

Preparation Example

Preparation of the Extract and Compound of the Invention

Air-dried and grounded rhizomes of *Coeloglossum. viride* (L.) Hartm. var. *bracteatum* (Willd.) Richter (5 kg) were extracted with eight volumes of 95% EtOH under heated for three times, filtered, and the filtrates are combined, then the solvent was removed under reduced pressure to give a residue (220 g). The residue was suspended in water and then partitioned with EtOAc. The water phase was subjected to column chromatography over macroporous resin, successively eluting with $H_2O$, and 20%, 40% and 80% EtOH in $H_2O$. The 20% and 40% EtOH-eluted solution was concentrated to give a residue (29 g) that was chromatographed over reversed-phase silica gel RP-18, eluting with a gradient increasing in MeOH in $H_2O$ (0-60%), to give several fractions based on TLC analysis. These fractions were further purified by a recrystallization, silica gel chromatography, Sephadex LH 20, and reversed phase preparative HPLC techniques to yield compounds W1 (70 mg), W2 (95 mg), W3 (85 mg), W4 (173 mg), W5 (65 mg), W6 (4.2 g), W7 (4.8 g), W8 (3.4 g), and W9 (1.2 g). The diagram of the isolation procedure see FIG. 1.

Pharmacology Experiments:

Example 1

Effects of CE and Compounds W6, W7, W8, W9 on Passive Avoidance Task Performance Impairment Caused by Scopolamine Study Objective:

Scopolamine, a muscarinic cholinergic receptor antagonist, has been shown to impair memory retention when given to mice shortly before training in passive avoidance task, the scopolamine-amnesia test is widely used as primary screening test for so-called anti-Alzheimer drugs. The present study was designed to investigate whether CE and W6-W9 could modulate the memory impairment induced by scopolamine, using step-down type passive avoidance tasks in mice.

Method:

Male ICR mice, 24-28 g, were used. The mice were housed for 2 days period of habituation before experiment. Mice were randomized into groups (n=20).

The mice were administered by gavage of physiological saline, or drugs at different doses, respectively in the negative control, scopolamine group, and test drugs groups. Twice daily for 2 days.

At D3, 30 min after administration of test drugs, scopolamine (1 mg/kg i.p) was administered, except for the control group.

30 min later, each mouse was individually placed onto the safety platform in the box of step-down apparatus. When the mouse stepped down and touched the grid floor, it was given an electric shock with a tension of 36V, and jumped back onto the rubber platform. Each animal was trained for 5 min and returned to the home cage.

24 hours after the learning trial, the animal was again placed on the platform and the step-down latency and the number of step-down events (number of errors) during 5 min were recorded. The results are shown in table 1.

Result:

The step-down test shows the latency time reduced significantly in the group of scopolamine relative to the control group, and the number of errors during 5 min was increased markedly. It was shown that scopolamine, at the dosage of 1 mg/kg, can impair the capacity of learning and memory in animal. CE, W6, W7, W8 or W9 treatment inhibited the reduction of the step-down latency and decreased the number of errors during the test session, attenuated the scopolamine-induced impairment of passive avoidance behaviors. The data indicated that all of CE, W6, W7, W8 and W9 can ameliorate impairment of passive avoidance induced by scopolamine.

TABLE 1

Effects of CE and W6-W9 on passive avoidance task performance impairment caused by scopolamine in mice (step-down test).

| Group | Dose (mg/kg) | Latency (s) | Number of errors |
|---|---|---|---|
| Control | | 266 ± 20 | 0.2 ± 0.1 |
| Scopolamine | | 147 ± 32# | 1.7 ± 0.4## |
| CE | 2.5 | 218 ± 19* | 0.2 ± 0.1** |
| | 5 | 245 ± 22* | 0.4 ± 0.2* |
| | 10 | 280 ± 27** | 0.6 ± 0.2* |
| W6 | 0.03 | 283 ± 38** | 0.2 ± 0.1** |
| | 0.3 | 259 ± 34* | 0.4 ± 0.2* |
| | 3 | 258 ± 17* | 0.3 ± 0.1* |
| W7 | 0.25 | 205 ± 142 | 0.4 ± 0.7* |
| | 1 | 237 ± 125* | 0.2 ± 0.4** |
| W8 | 0.25 | 197 ± 144 | 0.7 ± 0.9 |
| | 1 | 218 ± 127* | 0.3 ± 0.5* |
| W9 | 0.25 | 140 ± 129 | 0.8 ± 0.7 |
| | 1 | 210 ± 134* | 0.4 ± 0.5* |

Data represents mean ± S.E.M, n = 20 for each group.
P < 0.05,
P < 0.01 vs. control;
*P < 0.05,
**P < 0.01 vs. scopolamine group only.

Example 2

Effects of CE and W6 on Passive Avoidance Task Performance Impairment Caused by Cycloheximide (CHX)

Study Objective:

Cycloheximide is an inhibitor of protein synthesis. It can impair the performance of experimental animals in a wide variety of learning and memory tasks, including passive avoidance. In this experiment, the effect of W6 and CE on cycloheximide-induced memory deficit in the passive avoidance task was investigated.

Method:

The randomization and the administration of drugs are as before. The mice were administered with cycloheximide (120 mg/kg i.p), except for the control group. 30 min later, each mouse was individually placed onto the platform of the step-down apparatus, and trained for 5 min. The retention test started 24 hours later, the step-down latency and the number of step-down events (number of errors) during 5 min were recorded.

Results:

Cycloheximide (120 mg/kg, ip.) significantly impaired the acquisition of learning when given before the training trial. CE and W6 significantly reversed the cycloheximide-induced reduction of step-down latency, and decrease the number of errors. The result indicates that CE and W6 can ameliorate impairments of passive avoidance induced by cycloheximide, and increase learning and memory performance of mice. The results are shown in table 2.

TABLE 2

Effect of CE and W6 on impairment of passive avoidance behaviours induced by cycloheximide in mice (step-down test)

| Group | Dose (mg/kg) | Latency (s) | Improvement (%) | No. of errors |
|---|---|---|---|---|
| Control | | 255 ± 16 | | 0.2 ± 0.1 |
| Cycloheximide | | 174 ± 20### | | 1.0 ± 0.2### |
| CE | 2.5 | 183 ± 31 | 11 | 0.7 ± 0.2 |
| | 5 | 217 ± 20 | 53 | 0.5 ± 0.1** |
| | 10 | 231 ± 33 | 70 | 0.4 ± 0.1* |
| Control cycloheximide | | 276 ± 17 | | 0.1 ± 0.3 |
| | | 124 ± 30### | | 1.6 ± 1.9## |
| W6 | 1.25 | 211 ± 31 | 57 | 0.6 ± 1.2 |
| | 2.5 | 223 ± 24* | 65 | 0.7 ± 0.9* |
| | 5 | 182 ± 33 | 38 | 0.4 ± 0.5** |
| | 10 | 216 ± 29* | 61 | 0.3 ± 0.5** |

Data represents mean ± SEM, n = 20 for each group.
P < 0.01,
P < 0.001 vs. control;
*P < 0.05,
**P < 0.01 vs. cycloheximide only group.

Example 3

Effects of CE and W6 on Impairment of Learning and Memory Performance Caused by Aβ in Mice Study Objective:

Beta-Amyloid peptide (A beta), a 39-43 amino acid peptide, is believed to induce oxidative stress and inflammation in the brain, which are postulated to play important roles in the pathogenesis of Alzheimer's disease. Ample experimental evidence indicates that intracerebral injection or infusion of amyloid-beta peptides (Aβ) to rodents induces learning and memory impairments as well as neurodegeneration in brain areas related to cognitive function. In the present study, we assessed the effects of long-term oral administration of CE and W6 on a single intracerebroventricular (i.c.v.) injection in mice and intra-hippocampus injection in rats of aggregated beta-amyloid peptide 1-42 (Aβ(1-42))-induced memory impairment.

Method:

Aβ(1-42) (10 μg/mouse) was administered via ICV injection. The sham group was given same volumn of Ringer's solution. One week later, The mice with injection of Aβ(1-42) were randomly divided into 3 groups, and were administered by oral with saline, CE (5 mg/kg) or W6 (1 mg/kg), respectively. Two weeks later, step-down test and water-maze test were performed for evaluating the capacity of learning and memory of mice.

Water-maze test: Each mouse was first placed on the stairs, then released into the water from position 1 and allowed 120 sec to find the stairs. The mouse received 2 trials per day for 3 days. The starting location varied from position 1 to position 2 and position 3 for the next 2 day. The distance and the dead end increased every day. In D4, the mouse was put into water from position 3, the time to escape from water to the stairs and the number of entering the dead ends (number of errors) were measured. This method is used to evaluate the spatial performance and learning and memory performance of animal.

This experiment was repeated for CE with male Wistar rats. The protocal is almost the same, except Aβ(1-42) (10 μg/each side) was injected into hippocampus. The step-down test were performed for evaluating the capacity of learning and memory of rats.

Results:

ICV or intra-hippocampus injection of control mice with Aβ(1-42) impaired performance on the passive avoidance test (significantly decreased in step-down latency), and the water maze test (significantly prolonged the latency to escape from water and increased number of errors).

Treatment of mice or rats with CE and W6 for 2 weeks significantly blocked the Aβ(1-42)-induced impairment in passive avoidance performance, also significantly improved Aβ(1-42)-induced decrease in spatial working memory. These findings suggest that CE and W6 may have preventive effect against memory impairment related with Aβ of Alzheimer's disease.

TABLE 3

Effects of CE and W6 on Aβ(1-42)-induced impairment in passive avoidance performance in mice. (step-down test).

| Group | Dose (mg/kg) | Latency (s) | Number of errors |
|---|---|---|---|
| Sham | | 156 ± 35 | 1.3 ± 0.3 |
| Aβ only | | 30 ± 14## | 1.6 ± 0.2 |
| Aβ + CE | 5 | 118 ± 34* | 1.4 ± 0.3 |
| Aβ + W6 | 1 | 110 ± 37* | 0.9 ± 0.2 |

TABLE 4

Effects of CE and W6 on Aβ(1-42)-induced impairment of learning and memory in mice. (water-maze test)

| Group | Dose (mg/kg) | Escape Latency (s) | Number of errors |
|---|---|---|---|
| Sham | | 34 ± 8 | 4.3 ± 1.1 |
| Aβ only | | 62 ± 10# | 6.4 ± 1.1# |
| Aβ + CE | 5 | 36 ± 10* | 3.1 ± 1.4* |
| Aβ + W6 | 1 | 46 ± 11 | 3.1 ± 0.8* |

TABLE 5

Effect of CE on Aβ(1-42)-induced impairment in passive avoidance performance in rat. (step-down test)

| Group | Dose (mg/kg) | Latency (s) | Number of errors |
|---|---|---|---|
| Sham | | 241 ± 39 | 0.2 ± 0.1 |
| Aβ only | | 107 ± 34# | 1.3 ± 0.3# |
| Aβ + CE | 1.25 | 188 ± 69* | 0.4 ± 0.2 |
| | 5.0 | 237 ± 42* | 0.2 ± 0.1* |

Data represents mean ± SEM, n = 12-15.
$P < 0.05$,
$P < 0.01$ vs. sham group.
*$P < 0.05$, vs. Aβ only group.

Example 4

Effects of CE and W6 on Memory Impairment Induced by the Model of Vascular Dementia Study Objective:

It is well known that chronic cerebral hypoperfusion induced by permanent occlusion of bilateral common carotid arteries in animal is associated with behavioral and histopathological alterations. In this study, we investigated the effects of CE and W6 on learning and memory performance impairment caused by permanent occlusion of carotid arteries in mice and rats.

Method:

At surgery, under pentobarbital anaesthesia (40 mg/kg i.p.), the common carotid arteries of mice were exposed and occluded with thread permanently and the surrounding skin sutured. Sham-operated controls had their carotids exposed but not occluded. After 1 week, the survival mice with occluded carotids were randomly divided into 3 groups. 2 groups were repeated administered with CE (5 mg/kg, po) or W6 (1 mg/kg, po) daily. Four weeks after surgery, mice were trained and tested in a water maze and step-down apparatus.

This experiment was repeated for CE with male SD rats. The protocal is almost the same, except the Morris water maze test was used for rats.

Piracetam is the best known nootropic drug. It's mechanism of action is unknown but most would describe it as an intelligence booster and CNS (central nervous system) stimulant and is remarkably effective in counteracting cerebral hypoxia. Therefore, piracetam was used as a reference drug in this study.

Morris water maze test: Animals were tested in a water maze (Morris et al., 1982). After a habituation trial of 1 min on the first day, the animals were tested on the next three days for their ability to escape from the pool by searching for a 6 cm diameter perspex platform mounted 1.5 cm below the water level. Each rat received 4 escape trials every day, with the starting locations at fixed 2 positions. Immediately after the final escape trial, spatial bias was tested during a probe trial lasting 2 minute, during which the platform was removed and the number of animals crossings of the original platform position and the time spent in the original platform located quadrant within 2 min were recorded, as an index of the spatial learning and memory.

Results:

Four week's cerebral hypoperfusion in mice and rats caused deficits of learning and memory (step-down testing and water-maze testing). Long term treatment with CE and W6 significantly alleviated these changes in behavioral. Our data suggest the beneficial role of CE and W6 in cerebrovascular insufficiency states and dementia.

TABLE 6

Effects of CE and W6 on learning and memory performance impairment caused by permanent occlusion of 2 carotid arteries in mice. (step-down test)

| Group | Dose (mg/kg) | Latency (s) | Number of errors |
|---|---|---|---|
| Sham | | 256 ± 40 | 0.3 ± 0.2 |
| 2-VO only | | 125 ± 38# | 0.9 ± 0.2# |
| 2-VO + CE | 5 | 245 ± 30* | 0.2 ± 0.2* |
| 2-VO + W6 | 1 | 253 ± 31* | 0.2 ± 0.1* |

TABLE 7

Effects of CE and W6 on learning and memory performance impairment caused by permanent occlusion of 2 carotid arteries in mice. (water-maze test)

| Group | Dose (mg/kg) | Escape Latency (s) | Number of errors |
|---|---|---|---|
| Sham | | 25 ± 14 | 4.0 ± 0.3 |
| 2-VO only | | 51 ± 24## | 7.5 ± 0.7# |
| 2-VO + CE | 5 | 22 ± 11*** | 4.3 ± 0.5* |
| 2-VO + W6 | 1 | 33 ± 19* | 5.4 ± 1.4 |

Data are expressed as mean ± SEM, n = 10-15.
$P < 0.05$,
$P < 0.01$ vs sham group.
*$P < 0.05$,
**$P < 0.01$,
***$P < 0.001$ vs 2-VO only group.

Example 5

Effect of CE on Learning and Memory Performance in Normal Mice

Study Objective:

This experiment is to observe whether CE could enhance the capacity of learning and memory in young normal mice.

Method:

Male ICR mice (24-28 g) were used. Mice was repeated administered with CE (1.25 and 5 mg/kg) for 3 days. Then 3 days' learning trial in water-maze for each mouse was performed. From D4 to D6, mouse was released into water from the starting point and the escape latency and number of entering dead ends were recorded.

Result:

Compared with normal mice, CE treatment shortened the escape latency of mice in water-maze testing, and the number of entering dead ends decreased significantly. The result indicates that CE can enhance the capacity of learning and memory in young normal mice. (see FIG. 2 and FIG. 3)

Example 6

An Acute Toxicity Study of CE and W6 in Mice

Method:

KM mice were used for this experiment. 10 male and 10 female mice were included in each group. CE (5 g/kg) or W6-W9 (0.5 g/kg) were given by oral or by i.p. The animals were observed carefully and their body weight were checked every 3 days within 2 weeks.

Conclusion:

After orally administered a single dose of CE at 5 g/kg, there is no animal dead and the body weight of animals is gained relative to normal mice.

The result is the same with W6, W7, W8 or W9 at 0.5 g/kg (i.p. or p.o.).

These results suggest that CE and W6-W9 have little or even no acute toxicity in mice.

Example 7

In Vivo Effect of CE and W6 on Acetylcholinesterase (AchE) Activity

Study Objective:

It is generally accepted that the physiological role of AchE is the rapid hydrolysis and inactivation of Ach. Inhibitors of AchE can be beneficial in the treatment of Alzheimer's dementia. The purpose of this assay is to determine the influence of CE and W6 on AchE activity.

Method:

Wistar rats were randomly divided into 5 groups (n=6): normal control, HupA (1 mg/kg), CE (5 mg/kg), W6 (5 mg/kg), and W6 (20 mg/kg). The rats were fasting over night and given a single oral dose of drugs. 1 hour later, the rats were decapitated, the forebrains were rapidly removed under ice bath, weighed and homogenized in 0.9% saline using a ultrasonic homogenizer to obtain 10% brain homogenate. The homogenate was centrifuged (6000 rpm) for 20 mins at low temperature, and retained the supernatant. Then the AchE activity was measured with an assay kit.

Result:

The data show that a single dose of CE or W6 to rats has no inhibition on activity of AchE. It indicates that the improvement of CE and W6 on cognitive function in animal is not mediated via anticholinesterase pathway.

TABLE 8

Effects of CE and W6 on activity of AchE in vivo

| group | AchE activity | inhibition (%) |
|---|---|---|
| control | 0.72 ± 0.18 | — |
| Hup A (1 mg/kg) | 0.48 ± 0.10* | 34 |
| CE (5 mg/kg) | 0.77 ± 0.20 | 0 |
| W6 (5 mg/kg) | 0.80 ± 0.16 | 0 |
| W6 (20 mg/kg) | 0.72 ± 0.16 | 0 |

What is claimed is:

1. A method for improving memory performance in an animal having Alzheimer's disease or vascular dementia, the method comprising:

administering to said animal a therapeutically effective dose of a derivative of a succinate ester of general formula (I), or a stereo-isomer or a pharmaceutically acceptable salt thereof:

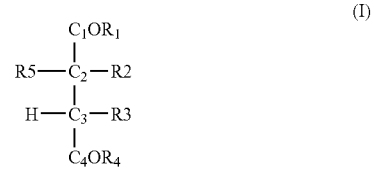

wherein, $R_1$ and $R_4$ are selected from —$OCH_3$, —OH, —O-Glu,

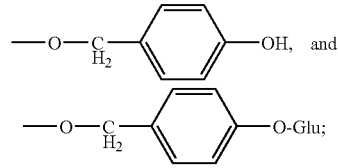

$R_2$ and $R_3$ are selected from H, —OH, —O-Glu,

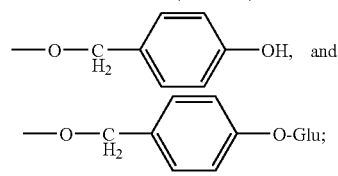

$R_5$ is selected from non-branched or branched $C_{1-6}$ alkyls; and the configuration of chiral center at C-2 and C-3 are 2R3S, 2R3R, 2S3S and 2S3R respectively.

2. The method according to claim 1, characterized in that said compound of formula (I) is:

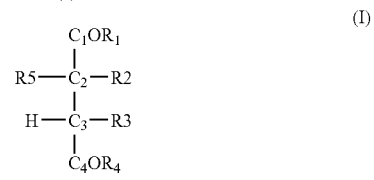

or a stereo-isomer or a pharmaceutically acceptable salt thereof, wherein $R_5$ is selected from the group consisting of methyl, ethyl, propyl, isopropyl, n-butyl, isobutyl, tert-butyl; and $R_1$, $R_2$, $R_3$, and $R_4$ are the same as that in claim 1.

3. The method according to claim 2 characterized in that said compounds include:

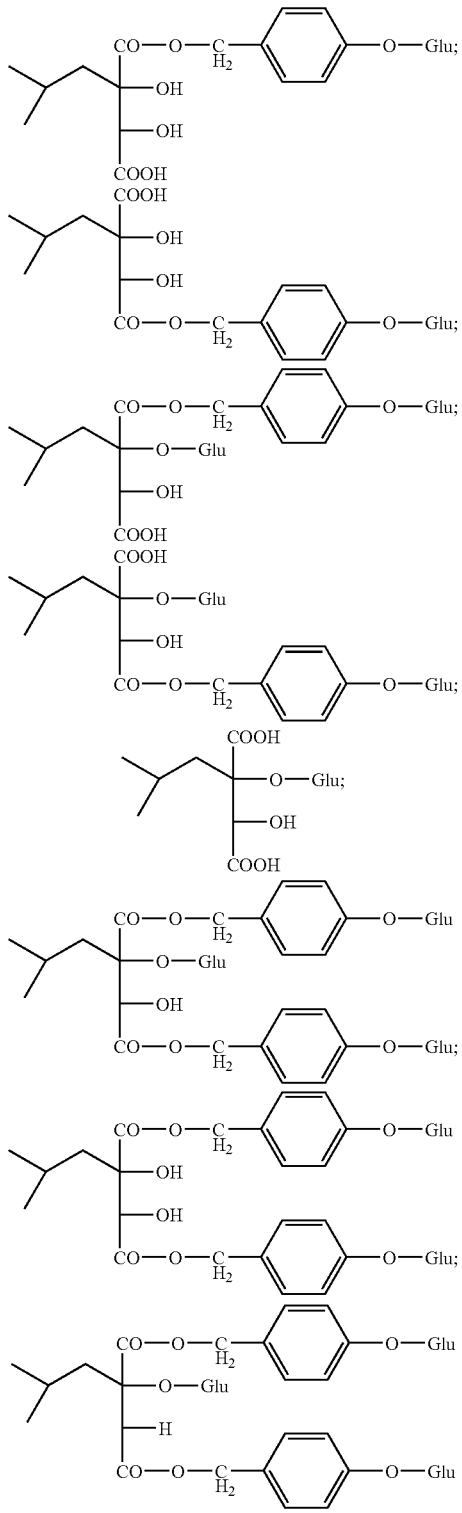

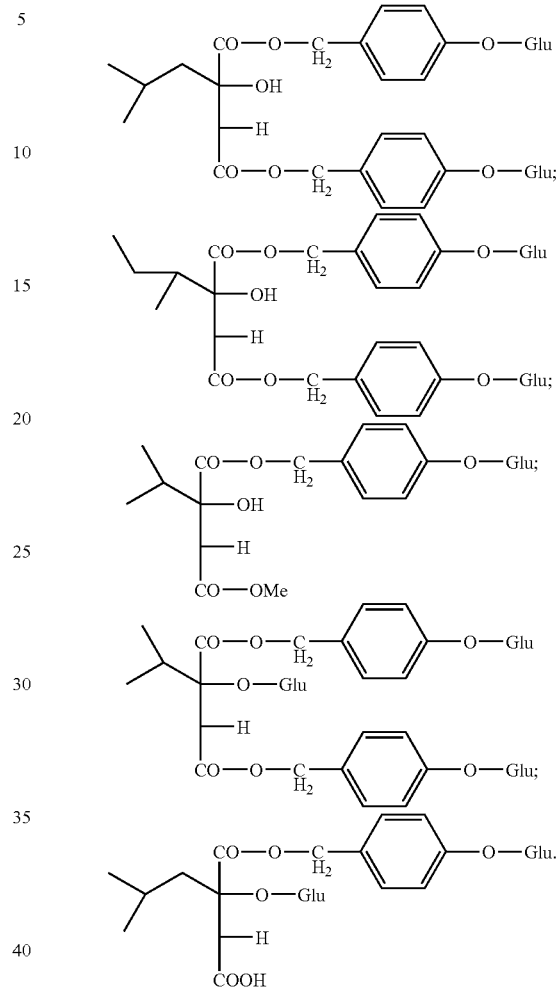

1,4-bis(β-D-glucopyranosyloxybenzyl)-2-β-D-glucopyranosyl-2-isobutylmalate (dactylorhin A) (W8);

and stereo-isomers and pharmaceutically acceptable salts thereof.

4. The method according to claim 1, wherein the compound is a pharmaceutically acceptable salt.

5. A method for improving memory performance in an animal having Alzheimer's disease or vascular dementia comprising:
administering to said animal a therapeutically effective dose of an extract of *Coeloglossum viride* (L.) Hartm. var. *bracteatum* (Willd.) Richter, said extract comprising ethanol soluble compounds.

6. The method according to claim 2, wherein the compound is a pharmaceutically acceptable salt.

7. The method according to claim 3, wherein the compound is a pharmaceutically acceptable salt.

8. The method of claim 5, wherein the extract is prepared from rhizomes.

9. The method of claim 5, wherein the animal is a human.

10. The method of claim 5, further comprising administering at least one of: scopolamine, cycloheximide, and amyloid-beta peptides.

* * * * *